US009126026B2

(12) United States Patent
Fisher

(10) Patent No.: US 9,126,026 B2
(45) Date of Patent: Sep. 8, 2015

(54) RAPID EXCHANGE BALLOON CATHETER WITH BRAIDED SHAFT

(75) Inventor: Beau M. Fisher, Danville, CA (US)

(73) Assignee: Innovation Holdings LLC, Irvine, CA (US)

(*) Notice: Subject to any disclaimer, the term of this patent is extended or adjusted under 35 U.S.C. 154(b) by 0 days.

(21) Appl. No.: 13/560,614

(22) Filed: Jul. 27, 2012

(65) Prior Publication Data

US 2012/0289898 A1 Nov. 15, 2012

Related U.S. Application Data

(63) Continuation of application No. 11/069,423, filed on Feb. 28, 2005, now Pat. No. 8,252,014.

(60) Provisional application No. 60/550,570, filed on Mar. 3, 2004.

(51) Int. Cl.
*A61M 25/10* (2013.01)
*A61M 25/00* (2006.01)
*A61M 25/01* (2006.01)

(52) U.S. Cl.
CPC ........... *A61M 25/104* (2013.01); *A61M 25/005* (2013.01); *A61M 25/0045* (2013.01); *A61M 25/0053* (2013.01); *A61M 2025/0059* (2013.01); *A61M 2025/018* (2013.01); *A61M 2025/0183* (2013.01)

(58) Field of Classification Search
CPC ...................... A61M 25/0012; A61M 25/0013; A61M 25/005; A61M 25/0054; A61M 25/10; A61M 25/0034; A61M 25/0036

USPC ........... 604/96.01, 103.04, 103.09, 523, 524, 604/526–527; 606/194
See application file for complete search history.

(56) References Cited

U.S. PATENT DOCUMENTS

| 3,965,909 A | 6/1976 | Waddell et al. |
| 4,425,919 A | 1/1984 | Alston et al. |
| 4,516,972 A | 5/1985 | Samson |
| 4,650,466 A | 3/1987 | Luther |
| 4,706,670 A | 11/1987 | Andersen et al. |
| 4,748,982 A | 6/1988 | Horzewski et al. |

(Continued)

FOREIGN PATENT DOCUMENTS

| DE | 3442736 C2 | 6/1986 |
| EP | 0203945 A1 | 12/1986 |

(Continued)

OTHER PUBLICATIONS

Meier, B., "Magnarail Probing Catheter: New Tool for Balloon Recanalization of Chronic Total Coronary Occlusions" J. Invasive Cardiol (1990) Nov.-Dec. 2: 227-229.

(Continued)

*Primary Examiner* — Quynh-Nhu H Vu
(74) *Attorney, Agent, or Firm* — Hamre, Schumann, Mueller & Larson, P.C.

(57) ABSTRACT

A balloon catheter for use alone or as a stent delivery system includes a balloon segment and a shaft segment having a varying flexibility. The shaft segment includes a polymer encased braid which extends along substantially the entire length of the shaft segment for added pushability and kink resistance. A flexible distal tip extends from the balloon for improved trackability.

2 Claims, 4 Drawing Sheets

(56) References Cited

U.S. PATENT DOCUMENTS

| | | | |
|---|---|---|---|
| 4,762,129 A | 8/1988 | Bonzel | |
| 4,764,324 A | 8/1988 | Burnham | |
| 4,771,777 A | 9/1988 | Horzewski et al. | |
| 4,898,591 A | 2/1990 | Jang et al. | |
| 4,943,278 A | 7/1990 | Euteneuer et al. | |
| 4,961,731 A * | 10/1990 | Bodicky et al. | 604/264 |
| 4,988,356 A | 1/1991 | Crittenden et al. | |
| 5,002,531 A | 3/1991 | Bonzel | |
| 5,037,404 A | 8/1991 | Gold et al. | |
| 5,040,548 A | 8/1991 | Yock | |
| 5,061,273 A | 10/1991 | Yock | |
| 5,147,302 A | 9/1992 | Euteneuer et al. | |
| 5,154,725 A | 10/1992 | Leopold | |
| 5,156,594 A | 10/1992 | Keith | |
| 5,180,367 A * | 1/1993 | Kontos et al. | 604/101.04 |
| 5,217,482 A | 6/1993 | Keith | |
| 5,221,270 A * | 6/1993 | Parker | 604/527 |
| 5,232,445 A | 8/1993 | Bonzel | |
| 5,267,958 A | 12/1993 | Buchbinder et al. | |
| 5,300,085 A | 4/1994 | Yock | |
| 5,312,356 A | 5/1994 | Engelson et al. | |
| 5,328,472 A | 7/1994 | Steinke et al. | |
| 5,338,295 A | 8/1994 | Cornelius et al. | |
| 5,346,505 A | 9/1994 | Leopold | |
| 5,350,395 A | 9/1994 | Yock | |
| 5,364,376 A | 11/1994 | Horzewski et al. | |
| 5,383,853 A | 1/1995 | Jung et al. | |
| 5,387,225 A | 2/1995 | Euteneuer et al. | |
| 5,395,332 A | 3/1995 | Ressemann et al. | |
| 5,395,334 A | 3/1995 | Keith et al. | |
| 5,410,797 A | 5/1995 | Steinke et al. | |
| 5,425,711 A | 6/1995 | Ressemann et al. | |
| 5,451,233 A | 9/1995 | Yock | |
| 5,458,639 A | 10/1995 | Tsukashima et al. | |
| 5,468,225 A * | 11/1995 | Teirstein | 604/103.04 |
| 5,496,275 A | 3/1996 | Sirhan et al. | |
| 5,496,346 A | 3/1996 | Horzewski et al. | |
| 5,501,227 A | 3/1996 | Yock | |
| 5,507,768 A | 4/1996 | Lau et al. | |
| 5,520,647 A | 5/1996 | Solar | |
| 5,522,818 A | 6/1996 | Keith et al. | |
| 5,533,987 A | 7/1996 | Pray et al. | |
| 5,538,510 A | 7/1996 | Fontirroche et al. | |
| 5,549,556 A | 8/1996 | Ndondo-Lay et al. | |
| 5,567,203 A | 10/1996 | Euteneuer et al. | |
| 5,569,199 A | 10/1996 | Solar | |
| 5,571,094 A | 11/1996 | Sirhan | |
| 5,575,771 A | 11/1996 | Walinsky | |
| 5,626,600 A | 5/1997 | Horzewski et al. | |
| 5,658,251 A | 8/1997 | Ressemann et al. | |
| 5,674,208 A | 10/1997 | Berg et al. | |
| 5,685,312 A | 11/1997 | Yock | |
| 5,702,373 A | 12/1997 | Samson | |
| 5,720,724 A | 2/1998 | Ressemann et al. | |
| 5,728,063 A | 3/1998 | Preissman et al. | |
| 5,749,888 A | 5/1998 | Yock | |
| 5,769,868 A | 6/1998 | Yock | |
| 5,824,173 A | 10/1998 | Fontirroche et al. | |
| 5,860,963 A * | 1/1999 | Azam et al. | 604/528 |
| 5,980,486 A | 11/1999 | Enger | |
| 6,004,291 A | 12/1999 | Ressemann et al. | |
| 6,007,517 A | 12/1999 | Anderson | |
| 6,036,670 A | 3/2000 | Wijeratne et al. | |
| 6,036,715 A | 3/2000 | Yock | |
| 6,056,722 A | 5/2000 | Jayaraman | |
| 6,066,114 A | 5/2000 | Goodin et al. | |
| 6,071,273 A * | 6/2000 | Euteneuer et al. | 604/523 |
| 6,129,708 A | 10/2000 | Enger | |
| 6,143,013 A | 11/2000 | Samson | |
| 6,165,197 A | 12/2000 | Yock | |
| 6,196,995 B1 | 3/2001 | Fagan | |
| 6,221,090 B1 | 4/2001 | Wilson | |
| 6,273,879 B1 | 8/2001 | Keith et al. | |
| 6,375,774 B1 * | 4/2002 | Lunn et al. | 156/158 |
| 6,485,457 B1 * | 11/2002 | Hisamatsu et al. | 604/102.02 |
| 6,488,694 B1 | 12/2002 | Lau et al. | |
| 6,500,147 B2 | 12/2002 | Omaleki et al. | |
| 6,527,789 B1 | 3/2003 | Lau et al. | |
| 6,548,010 B1 * | 4/2003 | Stivland et al. | 264/482 |
| 6,575,993 B1 | 6/2003 | Yock | |
| 6,585,657 B2 | 7/2003 | Yock | |
| 6,592,548 B2 | 7/2003 | Jayaraman | |
| 6,605,057 B2 | 8/2003 | Fitzmaurice et al. | |
| 6,659,977 B2 | 12/2003 | Kastenhofer | |
| 6,669,665 B2 | 12/2003 | Jayaraman | |
| 6,685,720 B1 * | 2/2004 | Wu et al. | 606/192 |
| 6,689,159 B2 | 2/2004 | Lau et al. | |
| 6,692,460 B1 | 2/2004 | Jayaraman | |
| 6,702,750 B2 | 3/2004 | Yock | |
| 6,733,473 B1 | 5/2004 | Reifart et al. | |
| 6,733,487 B2 | 5/2004 | Keith et al. | |
| 6,746,423 B1 | 6/2004 | Wantink | |
| 6,800,065 B2 | 10/2004 | Duane et al. | |
| 6,837,869 B2 | 1/2005 | Hamilton et al. | |
| 6,866,660 B2 | 3/2005 | Garabedian et al. | |
| 6,887,219 B2 | 5/2005 | Wantink | |
| 6,890,317 B2 | 5/2005 | Gerdts et al. | |
| 6,890,318 B2 | 5/2005 | Wantink | |
| 6,905,477 B2 | 6/2005 | McDonnell et al. | |
| 6,921,411 B2 | 7/2005 | Yock | |
| 6,953,470 B2 | 10/2005 | Holman et al. | |
| 7,001,358 B2 | 2/2006 | Fitzmaurice et al. | |
| 7,104,979 B2 | 9/2006 | Jansen et al. | |
| 7,297,302 B2 | 11/2007 | Berg et al. | |
| 7,455,739 B2 | 11/2008 | Zhou | |
| 7,507,229 B2 | 3/2009 | Hewitt et al. | |
| 7,615,043 B2 | 11/2009 | Zhou | |
| 7,632,288 B2 | 12/2009 | Wu | |
| 2001/0044648 A1 | 11/2001 | Wolinsky et al. | |
| 2003/0109886 A1 | 6/2003 | Keegan et al. | |
| 2003/0114794 A1 | 6/2003 | Duchamp | |
| 2003/0120208 A1 | 6/2003 | Houser et al. | |
| 2003/0187494 A1 | 10/2003 | Loaldi | |
| 2005/0065498 A1 | 3/2005 | McFerran | |
| 2005/0070879 A1 | 3/2005 | Coyle et al. | |
| 2005/0070880 A1 | 3/2005 | Varma et al. | |
| 2005/0107821 A1 | 5/2005 | Shanley et al. | |
| 2005/0113902 A1 | 5/2005 | Geiser et al. | |
| 2005/0124939 A1 * | 6/2005 | Konstantino | 604/194 |
| 2005/0171473 A1 | 8/2005 | Gerdts et al. | |
| 2005/0171570 A1 | 8/2005 | Yock | |
| 2005/0171571 A1 | 8/2005 | Goodin | |
| 2005/0234538 A1 | 10/2005 | Litvack et al. | |
| 2006/0009832 A1 | 1/2006 | Fisher | |
| 2012/0303054 A1 * | 11/2012 | Wilson et al. | 606/194 |
| 2013/0160932 A1 * | 6/2013 | Simpson et al. | 156/165 |

FOREIGN PATENT DOCUMENTS

| | | |
|---|---|---|
| EP | 0274129 B1 | 5/1992 |
| EP | 0580845 B1 | 11/1998 |
| EP | 0634943 B1 | 3/1999 |
| EP | 0650740 B1 | 9/1999 |
| EP | 0821979 B1 | 1/2003 |
| EP | 1255506 B1 | 9/2003 |
| EP | 1340516 A1 | 9/2003 |
| EP | 1470834 A1 | 10/2004 |
| EP | 0925801 B1 | 11/2004 |
| EP | 1015065 B1 | 11/2004 |
| EP | 1182989 B1 | 12/2004 |
| EP | 0998955 B1 | 3/2005 |
| EP | 1207930 B1 | 6/2005 |
| EP | 1208815 | 8/2005 |
| EP | 1284779 B1 | 10/2005 |
| EP | 1234594 B1 | 2/2006 |
| EP | 1518582 B1 | 6/2008 |
| EP | 1120129 B1 | 10/2008 |
| EP | 1475125 B1 | 7/2010 |
| WO | WO 94/11053 A1 | 5/1994 |
| WO | WO 03/084592 A2 | 10/2003 |
| WO | WO 2004/045699 A1 | 6/2004 |
| WO | WO 2004/054651 A2 | 7/2004 |
| WO | WO 2004/112875 A1 | 12/2004 |
| WO | WO 2005/021080 A1 | 3/2005 |

(56) References Cited

FOREIGN PATENT DOCUMENTS

| WO | WO 2005/035044 A1 | 4/2005 |
|---|---|---|
| WO | WO 2005/084319 A1 | 9/2005 |
| WO | WO 2005/094931 A1 | 10/2005 |
| WO | WO 2005/094932 A1 | 10/2005 |
| WO | WO 2006/017057 A2 | 2/2006 |

OTHER PUBLICATIONS

Kaltenbach, M., et al., "Long Wire Technique—Experience with 100 Procedures" Z Kardiol (1987) 76 Suppl 6: 53-57.

Medina, A., et al., "Use of Bonzel's Monorail Balloon Catheter in the Practice of Coronary Angioplasty" Rev. Esq. Cardiol (1986) Nov.-Dec. 39: 404-406.

Freitas, A.D., at al., "Coronary Transluminal Angioplasty and Determination of the Intracoronary Gradient with a New Monorail System" rev Port Cardiol (1989) Oct. 8: 699-702.

Bonzel, T et al., "Seven Years Development and Application of the Sliding Rail System (Monorail) for PTCA", The Pratice of Interventional Cariology ($2^{nd}$ Edition), Mar. 12, 2004.

Vogel, John H.K., et al., The Practice of Interverntional Cardiology, Mosby Year Book, Second Edition, (1993).

Meier, B., Technology of Current Dilatation Systems and Methodological Procedures Kardiologie, 76: Suppl. 6, 5-10 (1987).

\* cited by examiner

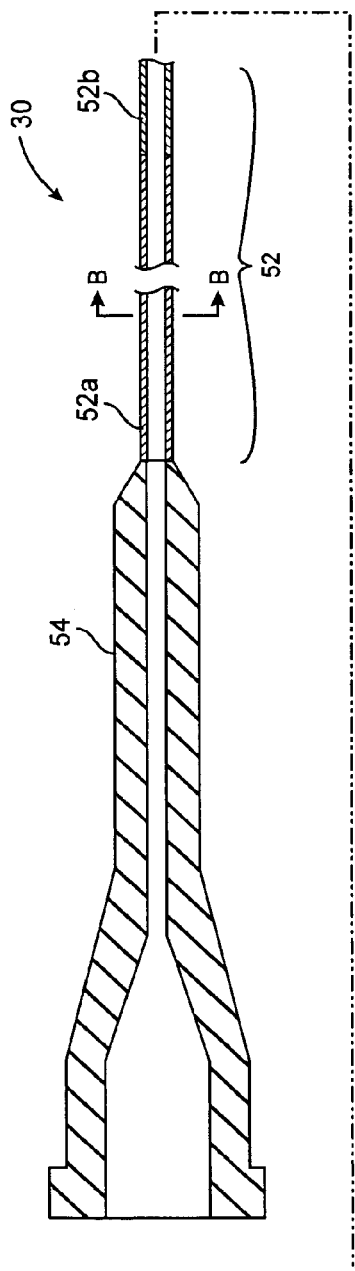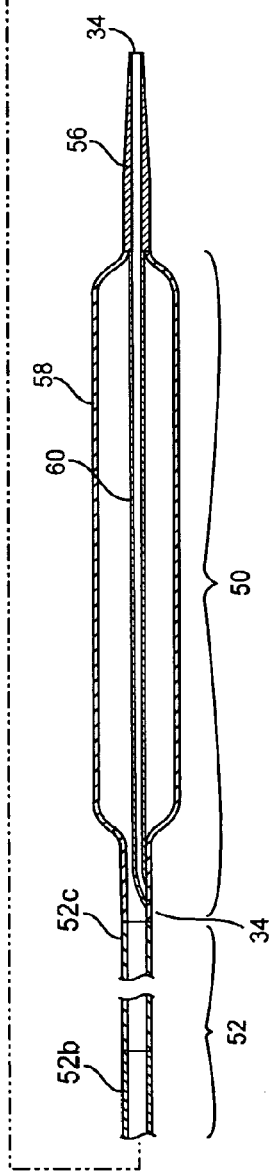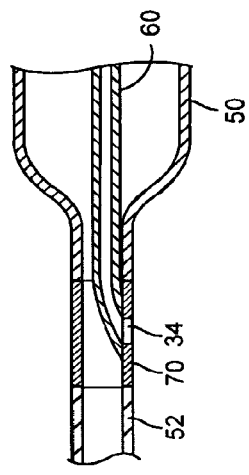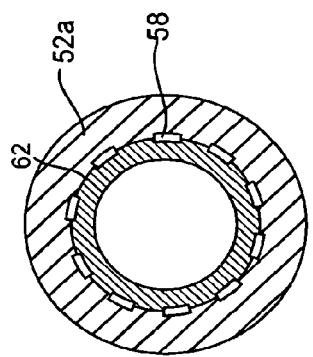
FIG. 2A
FIG. 2B
FIG. 3

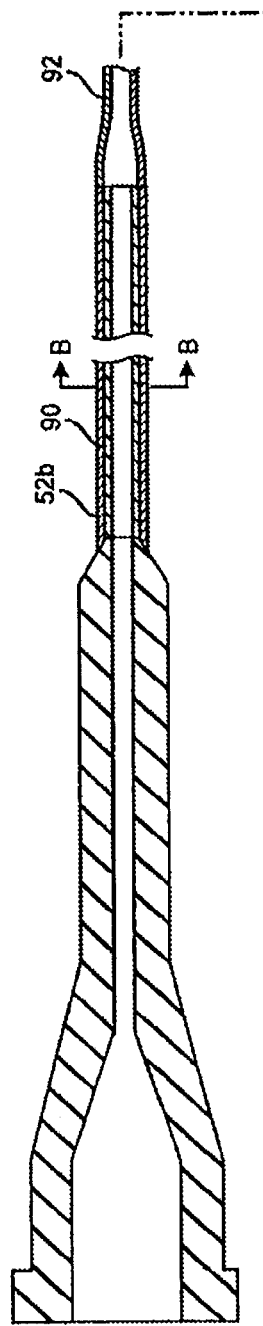
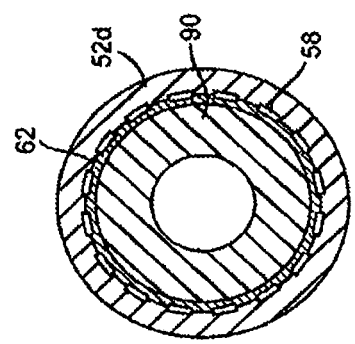
FIG. 5B
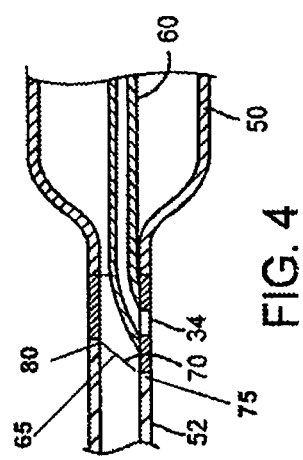
FIG. 4
FIG. 5A

RAPID EXCHANGE BALLOON CATHETER WITH BRAIDED SHAFT

CROSS-REFERENCE TO RELATED APPLICATIONS

This application is a continuation of, and claims the benefit of priority under 35 USC §120 to, U.S. patent application Ser. No. 11/069,423, filed on Feb. 28, 2005, which claims the benefit of priority under 35 USC §119 to provisional application Ser. No. 60/550,570 filed on Mar. 3, 2004, which applications are incorporated in their entirety by express reference herein.

BACKGROUND

Rapid exchange balloon catheters are described in U.S. Pat. Nos. 4,762,129 and 5,040,548 which are incorporated herein by reference. These rapid exchange catheters include a distal guidewire lumen which extends through the balloon from a distal end of the balloon to a guidewire exit port proximal of the balloon. In these and other known rapid exchange balloon catheter systems the catheter shafts include a proximal stiff catheter section extending along about 75% of the catheter length and a distal more flexible portion of the catheter between the stiff section and the balloon. The portion of the catheter proximal of the balloon and distal to the stiffer proximal catheter section should be simultaneously very flexible to navigate the coronary arteries, have good column strength to provide pushability, and have good kink resistance. The proximal catheter section generally requires good column strength and less flexibility.

Hypotubes or small metal tubes have been used for the proximal sections of rapid exchange catheters due to their excellent pushability and small wall thickness. Braided catheters can also been used for improved kink resistance.

SUMMARY OF THE INVENTION

The present invention relates to rapid exchange balloon catheter having a braid to provide pushability and kink resistance while maintaining flexibility.

In accordance with one aspect of the invention, a balloon catheter comprises a balloon segment having an expandable balloon and a guidewire tube extending through the balloon, the guidewire tube having a proximal port near a proximal end of the balloon and a distal port near a distal end of the balloon, a shaft segment connected to a proximal end of the balloon segment, the shaft segment including a polymer encased braid with an inflation lumen extending from a proximal end of the distal segment to the interior of the balloon segment, and a hypotube located within a proximal portion of the shaft segment.

In accordance with another aspect of the invention, a balloon catheter comprises a balloon segment having an expandable balloon and a guidewire tube extending through the balloon, the guidewire tube having a proximal port near a proximal end of the balloon and a distal port near a distal end of the balloon, a shaft segment connected to a proximal end of the balloon segment, the shaft segment including an inflation lumen extending from a proximal end of the distal segment to the interior of the balloon segment, and a flexible distal tip extending distally of the balloon segment, the distal tip formed of a material different from the balloon segment.

In accordance with a further aspect of the invention, a balloon catheter comprises a balloon segment having an expandable balloon and a guidewire tube extending through the balloon, the guidewire tube having a proximal port near a proximal end of the balloon and a distal port near a distal end of the balloon, a shaft segment connected to a proximal end of the balloon segment, the shaft segment comprising a polymer encased braid with an inflation lumen extending from a proximal end of the distal segment to the interior of the balloon segment, and a distal end of the braid cut at an angle with respect to a longitudinal axis of the shaft segment, and a tip of the angle cut braid extending distally at least to the proximal port of the guidewire tube.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 2A is a cross sectional side view of a rapid exchange balloon catheter.

FIG. 2B is a cross section of the catheter of FIG. 2A taken along line B-B of FIG. 2A.

FIG. 3 is a side cross sectional view of a portion of one embodiment of a rapid exchange catheter with a transition sleeve interconnecting the shaft segment and the balloon segment of the catheter.

FIG. 4 is a side cross sectional view of a portion of one embodiment of a rapid exchange catheter with an angle cut distal end of a braided shaft segment.

FIG. 5A is a cross sectional side view of a rapid exchange balloon catheter with a shaft segment having a combination of braid and hypotube.

FIG. 5B is a cross section of the catheter of FIG. 5A taken along line B-B of FIG. 5A.

DETAILED DESCRIPTION

Figure 1:
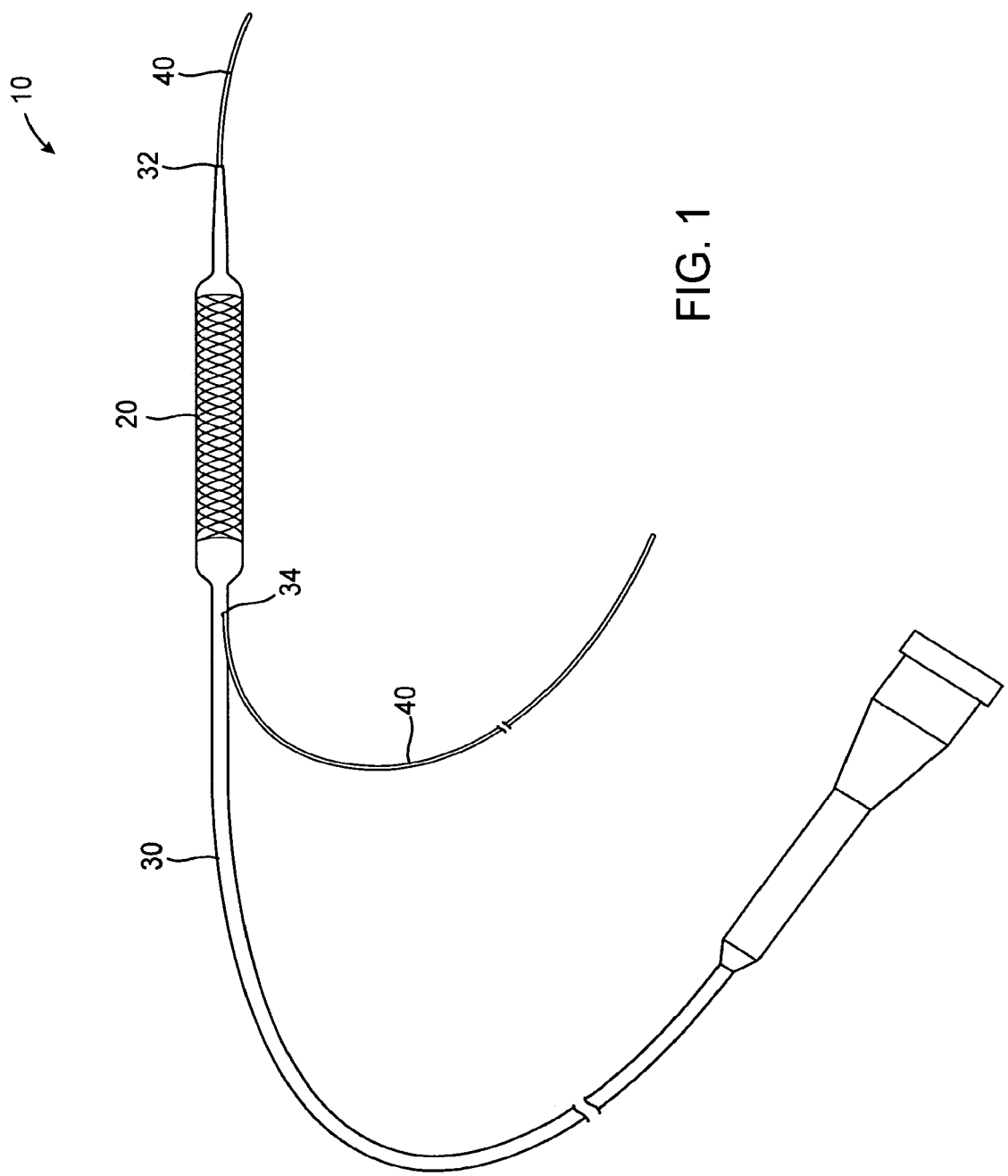
FIG. 1 is a side view of stent delivery system including a stent, a rapid exchange balloon catheter, and a guidewire.

The stent delivery system 10 of FIG. 1 includes a stent 20 (shown schematically), a rapid exchange balloon catheter 30, and a guidewire 40. FIG. 1 shows the catheter and balloon in the expanded or inflated configuration. In the unexpanded or delivery configuration, the balloon and stent will have a diameter close to the diameter of the catheter shaft. As shown in FIG. 1, the catheter 30 has a distal guidewire port 32 at a distal end of the catheter and a proximal guidewire port 34 proximal of the balloon. The catheter 30 is inserted into a patient over the guidewire 40 by passing the guidewire into the distal port 32 of the catheter, through a guidewire lumen within the balloon and out the side opening 34 of the catheter.

FIG. 2A is an enlarged cross sectional view of the rapid exchange catheter 30 of FIG. 1. The catheter 30 includes a balloon segment 50, a shaft segment 52, a luer hub 54 or other filling for connection to a source of pressurized fluid for inflation of the balloon, and a flexible distal tip segment 56. The balloon segment 50 has an expandable balloon 58 and a guidewire tube 60 extending through the balloon. The guidewire tube 60 terminates at the proximal port 34 near a proximal end of the balloon and distal of the distal end of the balloon. The shaft segment 52 can be connected in multiple variations to a proximal end of the balloon segment 50 and varies in flexibility from a most flexible distal end to a stiffer proximal end. The pushability of the proximal end of the shaft segment 52 is more important than flexibility since this portion of the catheter will remain within a guide catheter along a path from the femoral artery access site to the vicinity of the heart along a path which is not particularly tortuous.

In the embodiment shown in FIG. 2A, the construction of the catheter shaft (i.e. catheter material) changes at two points to achieve the varying flexibility desired. However, the catheter can also include more or less material changes. The catheter also can employ diameter changes to achieve the varying flexibility. The catheter shaft 52 includes a braid which preferably extends substantially the entire length of the catheter shaft. The pick count of the braid can be varied along the length of the shaft 52 to achieve a desired variation in flexibility. In addition, the braid may be replaced by a coil having a constant or variable coil spacing.

The following example of a catheter shaft construction is given by way of example and not limitation. The catheter shaft 52 includes three segments moving from the proximal end, the shaft segments are segment 52a, segment 52b, and segment 52c. Segment 52a is formed of Grilamid or other stiff material (e.g. Grilamid TR55) and has an outer diameter of about 0.03 to about 0.055 inches, preferably about 0.04 to about 0.05 inches and an inner diameter of about 0.015 to about 0.030 inches, preferably about 0.02 inches. Segment 52b is formed of Pebax or other medium stiffness material (e.g. Pebax 75D) and has an outer diameter of about 0.025 to about 0.05 inches, preferably about 0.035 to about 0.05 inches and an inner diameter of about 0.015 to about 0.030 inches, preferably about 0.02 inches. Segment 55c is formed of Pebax or other flexible material (e.g. Pebax 35D) and has an outer diameter of about 0.02 to about 0.045 inches, preferably about 0.03 to about 0.04 inches and an inner diameter of about 0.015 to about 0.030 inches, preferably about 0.02 inches. Segment 52a generally has a length of about 90 to about 100 cm, while segments 52b and 52c have lengths of about 10 to about 20 cm. A length of the balloon 50 may be varied depending on a length of a stent to be delivered with the balloon.

The shaft segment 52 includes a polymer encased braid for added pushability and kink resistance. In one preferred embodiment, the braid extends along substantially the entire length of the shaft segment 52 from the luer hub 54 to the balloon segment 50. The braid may be formed by braiding any number of wires, for example, about 8 to 20 wires can be used. The wires can also be round, flat, or other shapes. In one preferred embodiment, as illustrated in FIG. 2B, the wires are rectangular flat wires 58, such as stainless steel or NiTi.

The braided shaft may be formed by forming a thin layer of polymer material inner layer over a shaft, braiding the wires over the polymer inner layer, placing the outer layers of the three or more different polymer shaft materials over the braid and thermally fusing the catheter to encase the braid in polymer. The polymer inner layer 62 is shown in FIG. 2B. Examples of the polymer inner layer include Teflon or Pebax materials.

The balloon 58 can be formed from a tube of nylon or other known balloon material by expanding the tube in a mold to form the shape of the balloon. In the embodiment shown in FIG. 2A, at least a portion of the proximal end of this tube which is used for formation of the balloon is left on the balloon for formation of the proximal guidewire port 34 and a thermal bond to the braided shaft 52.

The catheter described herein has an optional flexible distal tip 56 which provides improved delivery. A distal end of the balloon 58 and the guidewire tube 60 are fused together and are fused to a flexible material which forms the flexible distal tip 56. The flexible distal tip has a length of at least about 0.2 inches and preferably about 0.3 inches. The flexible distal tip can be formed of a material which is more flexible than the materials of the shaft and more flexible than the material of the balloon. For example, the distal tip may be formed of Pebax 35D. The flexible tip tapers to a smallest dimension at its distal end. The flexible distal tip can alternatively be formed from the balloon material, if the material is sufficiently tapered to increase flexibility.

The advantages of forming a flexible distal tip include improved tracking over a guidewire. During delivery of a standard catheter without a flexible distal tip, the catheter can tend to push the guidewire away from an initial guidewire path due to the much higher stiffness of the catheter than the guidewire. For example, the catheter could continue on a straight path down a main artery rather than curving along the guidewire in a branch artery which causes the guidewire to be moved out of position. With the flexible distal tip, the catheter stiffness at the distal tip is more closely matched to the guidewire stiffness which causes the distal tip to more closely follow the original path of the guidewire. The distal tip can also help to dilate narrow lumens allowing improved access.

FIG. 3 illustrates an alternative embodiment of a catheter in which the braided catheter shaft 52 is connected to the balloon 50 by a sleeve 70. The sleeve 70 without braid is used to form the bond between the balloon 50, the guidewire tube 60, and the braided shaft 52. The sleeve 70 is a relatively short segment of about 0.3 inches or less, preferably about 0.1 inches.

FIG. 4 illustrates another embodiment of a catheter in which a distal end 80 of the braided catheter shaft 52 is cut at an angle other than ninety degrees with respect to the longitudinal axis of the braded catheter shaft 52 and formed as a slanted line 65 when viewed in a cross section. When viewed in the cross section, the slanted line 65 includes an angle cut distal end 80 and an angle cut proximal end 75. The angle cut distal end 80 allows the braided catheter shaft 52 to be continued distally substantially to or past the proximal guidewire opening 34 to provide kink resistance. The angle cut proximal end 75 extends less distally toward the proximal guidewire opening 34 than the angle cut distal end 80.

FIGS. 5A and 5B illustrate an alternative embodiment of the catheter in which the braided catheter shaft 52 is formed in the manner described above with respect to FIG. 2A except that the proximal most shaft segment 52a of FIG. 2A is replaced with a shaft segment 52d in which the polymer and braid are formed over an entire or a portion of a stainless steel or other material hypotube 90. This design allows the use of a hypotube which has substantially no longitudinal compression with the typical axial force used in a catheter procedure. Thus, pushability can be increased. FIG. 5B illustrates the cross section of the hypotube and surrounding polymer encased braid 58.

The advantages of forming a polymer encased braid over the hypotube 90 include the ability to securely attach the braided catheter to the hypotube, the uniformity of construction and appearance of the finished catheter, and the elimination of the need for a transition member to prevent kinking at the distal end of the hypotube.

FIG. 5A also illustrates an optional tapered section 92 just distal of the hypotube which allows the use of a larger outer diameter hypotube section 52d and a smaller outer diameter on the braid only sections 52b and 52c.

Figure 6:
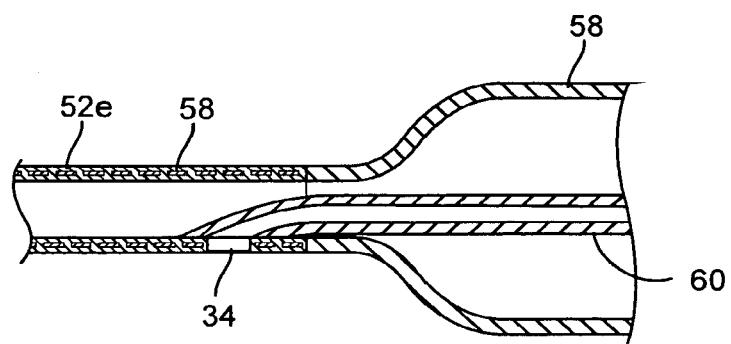
FIG. 6 is a side cross sectional view of a portion of another embodiment of a rapid exchange catheter with a braided shaft perforated for a proximal guidewire exit port.

FIG. 6 illustrates and alternative embodiment of the rapid exchange catheter in which braided shaft distal end segment 52e is perforated near its distal end to form the proximal guidewire opening. The inner guidewire tube 60 is then fused directly to the braided shaft 52e and the balloon 58 is connected directly to braided shaft. The perforating of the braided shaft 52e allows the braid 58 to extend all the way to the balloon providing kink resistance along the entire shaft. Any protruding ends of the braid 58 are encased with polymer during formation of the bond between the balloon 58, the guidewire tube 60, and the shaft 52*e*.

The drawings have illustrated the bonds between the different polymer materials used in the catheter as fused together along a line. In most cases the bonds will be formed by thermal welding and will actually appear as smooth transitions in which the materials are mixed at the fused region.

Although the catheter of the present invention has been described as a stent delivery system, the catheter may also be used as a dilation catheter, drug delivery catheter, or other catheter. In addition, the catheter described and shown herein has a distal guidewire opening spaced from the balloon at a distal end of the catheter and a proximal guidewire opening relatively closer to the balloon than the distal opening. This allows for a short exchange length improving exchange time. Other exchange lengths may also be used with the invention if desired.

While the invention has been described in detail with reference to the preferred embodiments thereof, it will be apparent to one skilled in the art that various changes and modifications can be made and equivalents employed, without departing from the present invention.

The invention claimed is:

1. A balloon catheter comprising:
   a balloon segment having an expandable balloon and a guidewire tube extending through the balloon, the guidewire tube having a proximal port near a proximal end of the balloon and a distal port near a distal end of the balloon, wherein the proximal port is located relatively closer to the proximal end of the balloon than the distal port;
   a braided shaft segment connected to a proximal end of the balloon by a sleeve, the braided shaft segment having an inflation lumen extending from a proximal end of the braided shaft segment to an interior of the balloon segment; and
   a distal end of the braided shaft segment being cut at an angle other than ninety degrees with respect to a longitudinal axis of the braided shaft segment and formed as a slanted line when viewed in a cross section,
   wherein when viewed in the cross section, the slanged line includes an angle cut distal end and an angle cut proximal end, and
   wherein the angle cut distal end allows the braided shaft segment to be continued distally to or past the proximal port to provide kind resistance; the angle cut proximal end extends less distally toward the proximal port of the guidewire tube than the angle cut distal end.

2. The balloon catheter of claim 1, wherein a distal tip of the cut end of the braid is positioned in the balloon catheter opposite the proximal port of the guidewire tube.

* * * * *